(12) United States Patent
Falus et al.

(10) Patent No.: US 8,741,845 B1
(45) Date of Patent: Jun. 3, 2014

(54) LYOPHILIZED FIBRIN SEALANT FOR HIGH VOLUME HEMORRHAGE

(71) Applicants: George David Falus, New York City, NY (US); Leonid Medved, Ellicott City, MD (US)

(72) Inventors: George David Falus, New York City, NY (US); Leonid Medved, Ellicott City, MD (US)

(73) Assignee: Biomedica Mangement Corporation, Halethorpe, MD (US)

( * ) Notice: Subject to any disclaimer, the term of this patent is extended or adjusted under 35 U.S.C. 154(b) by 0 days.

(21) Appl. No.: 13/731,126

(22) Filed: Dec. 31, 2012

Related U.S. Application Data

(63) Continuation-in-part of application No. 12/487,057, filed on Jun. 18, 2009, now Pat. No. 8,367,802.

(51) Int. Cl.
*A61K 38/36* (2006.01)
*A61K 9/70* (2006.01)
*C07K 14/745* (2006.01)

(52) U.S. Cl.
CPC . *A61K 38/36* (2013.01); *A61K 9/70* (2013.01); *C07K 14/745* (2013.01)
USPC ......... 514/14.9; 514/13.7; 530/381; 530/382; 530/384

(58) Field of Classification Search
None
See application file for complete search history.

(56) References Cited

U.S. PATENT DOCUMENTS

| | | | | | |
|---|---|---|---|---|---|
| 4,606,337 | A | * | 8/1986 | Zimmermann et al. | 602/48 |
| 4,829,995 | A | * | 5/1989 | Metters | 602/58 |
| 5,610,147 | A | * | 3/1997 | Seelich | 514/13.7 |

OTHER PUBLICATIONS

First aid for bleeding from the Red Crescent, downloaded Sep. 13, 2013.*

* cited by examiner

*Primary Examiner* — James H Alstrum Acevedo
*Assistant Examiner* — Fred Reynolds

(57) ABSTRACT

ClotBlock is a lyophilized fibrin hemostatic designed for use an adjunct or primary treatment in moderate to severe hemorrhage. It can be applied directly to the wound in a laparotomy procedure or as non-invasive sealant. Its crosslinking technology generates a strong and safe adhesive fibrin sealant required for high volume hemostasis. The attachment properties of the cake as well as the rapid formation of and stability of the fibrin clot ensures that a strong stable fibrin clot is formed within 1 to 5 minutes depending on the grade of the wound. The agent is safe, biocompatible, biodegradable and can be stored at room temperature for one year.

21 Claims, 7 Drawing Sheets

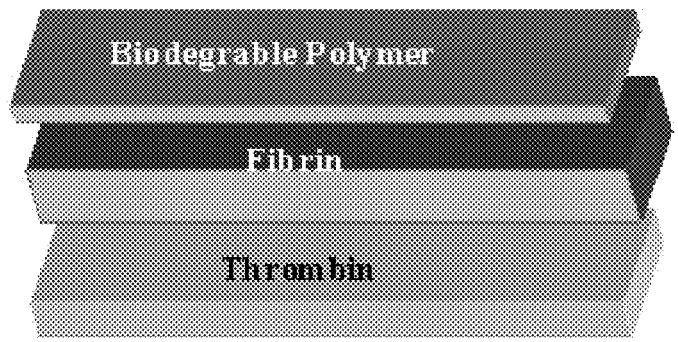
Figure 1. Three lawyer lyophilized block
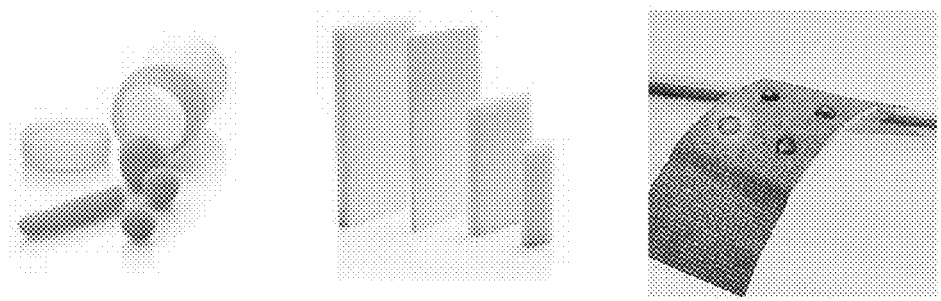
A Spheres and Cylinders        B. Block        C Bandage
Figure 2

1 – SeeBlue Plus2 protein standards (Invitrogen)
2 – CF + FXIIIa, 0 min
3 – CF + FXIIIa, 10 min
4 – CF + FXIIIa, 30 min
5 – CF + activa, 0 min
6 – CF + activa, 10 min
7 – CF + activa, 30 min
8 – CF + FXIIIa + activa, 0 min
9 – CF + FXIIIa + activa, 10 min
10 – CF + FXIIIa+ activa, 30 min Kidney  A  B Liver  A  B

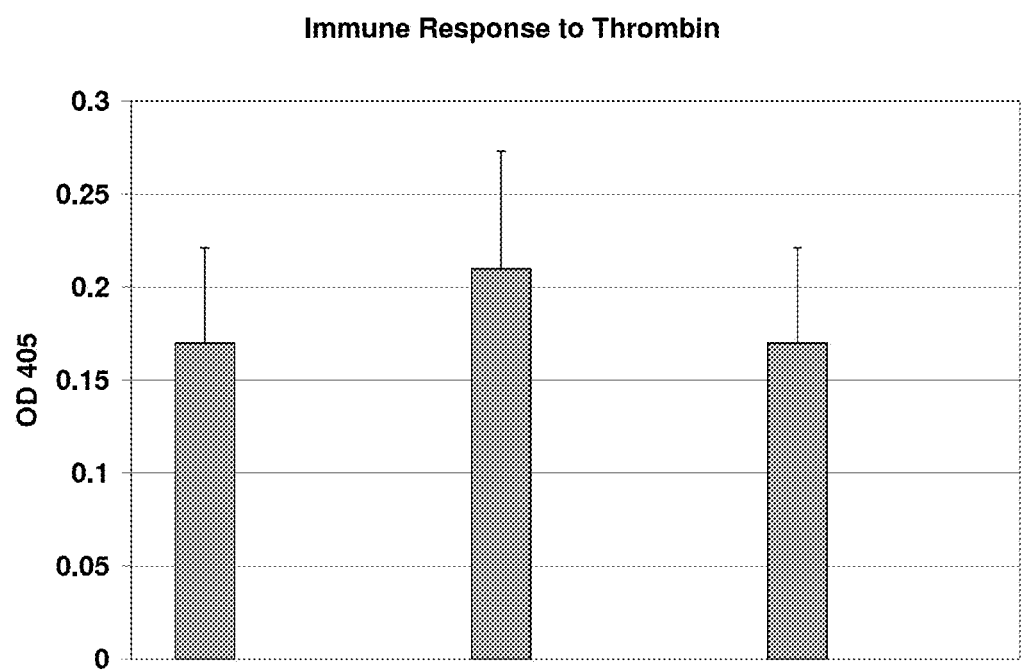
Figure 10
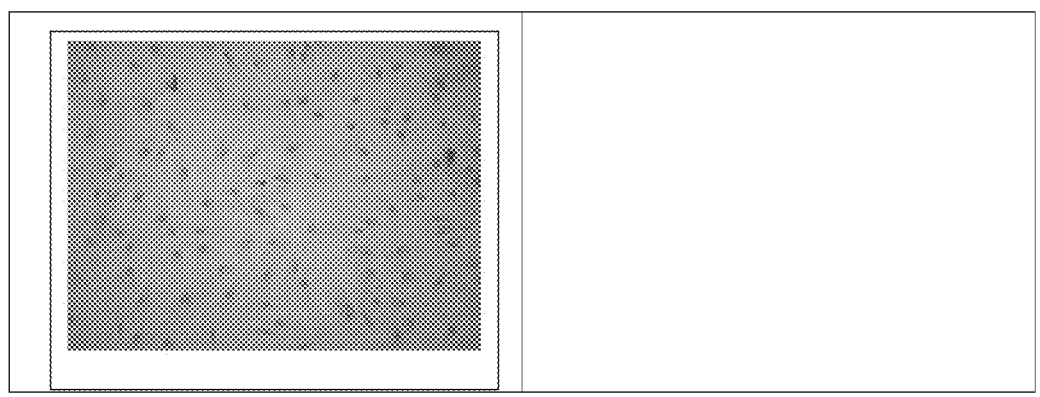
Figure 11    A    B

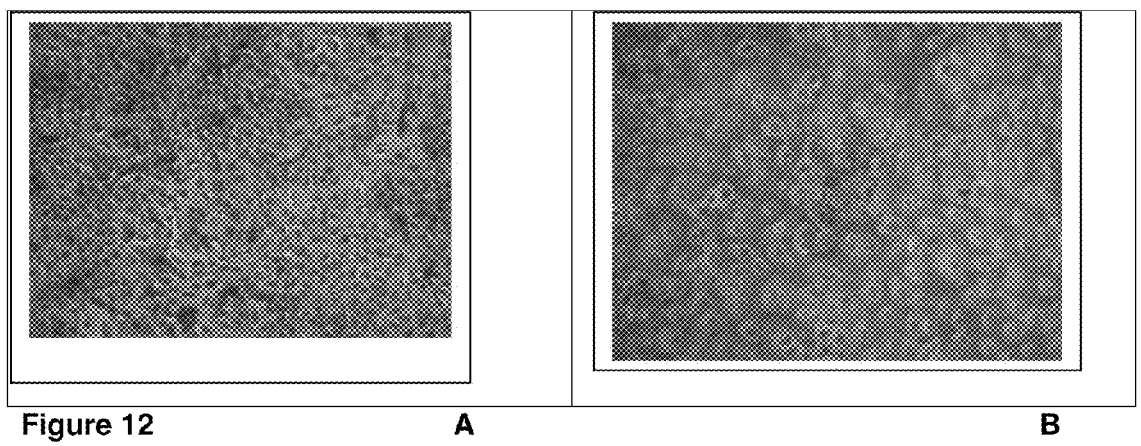
Figure 12     A     B

LYOPHILIZED FIBRIN SEALANT FOR HIGH VOLUME HEMORRHAGE

RELATED APPLICATIONS

This application is a Continuation-In-Part of U.S. patent application Ser. No. 12/487,057 (allowed) filed on Jun. 18, 2009 which has received a Notice of Allowance on Nov. 6, 2012 and with the Issue Fee to be paid before Feb. 6, 2013. All description, drawings and teachings set forth therein are expressly incorporated by reference herein and we claim priority upon the teachings expressly made therein.

FIELD OF THE INVENTION

The present invention is related to a method to produce a two component or bi-layer system consisting of a sterile biocompatible lyophilized desAB fibrin polymer or fibrin II polymer composition from concentrated desAB fibrin monomer or fibrin II monomer in acid solution, and lyophilized thrombin for application as an adhesive sealant component and hemostatic agent. The preparation (invention) trademarked ClotBlock is presented in various solid shapes and thickness that may be used to stop bleeding or seal tissue in vivo with and without compression. It is particularly related to need of affixing a fibrin Clot without a biodegradable support or a support that can be detached after application over a bleeding wound in order to seal tissue and control vascular, epidermal, bone or internal hemorrhage. The invention may include a biodegradable support made of hyaluronic acid or other biodegradable polymer,

BACKGROUND OF THE INVENTION

Severe bleeding for organ resection, trauma, or large dermal wounds is sometimes difficult to control. Recently fibrin-based patches have been tested to seal grade IV/V wounds using cellulose or gelatin supports. These technologies however cannot be applied to certain types of procedures such as interventional radiology, orthopedic or laparoscopic surgery. In addition the "support" used by these products remains in the body until biodegraded causing severe inflammatory reaction to foreign body.

Current Solutions and Limitations.

In general, the synthetic adhesives are used for the tight sealing of vessels or of lungs and for "gluing" the edges of skin incisions. These glues are eliminated, in general after the scaring of the wound, by biodegradation, absorption or by simple detachment in the form of scabs. Various technologies have been developed for the formulation of tissue adhesives. Some of them are of synthetic origin, such as the glues based on cyanoacrylates (2-butyl cyanoacrylate, 2-octyl cyanoacrylate), or synthetic polymers, and others contain biological materials such as collagen or fibrin which in addition have hemostatic properties.

As a result of their hemostatic and adhesive properties, sealants, and particularly fibrin sealants have been extensively used in most surgical specialties for over two decades to reduce blood loss and post-operative bleeding because of the ability to adhere to human tissue as they polymerize (1, 2, 3). These compounds are used to seal or reinforce the sealing of wounds that have been sutured or stapled; they can also be used with pressure over an injured area. Fibrin sealants are biological adhesives that mimic the final step of the coagulation cascade. (4) The main components of the sealant are fibrinogen, plasma proteins and factor XIII on the one hand and thrombin, and calcium chloride on the other. The components are often extracted from human plasma or produced by recombinant techniques. Mixing fibrinogen and thrombin creates a polymer barrier (fibrin) that simulates the last stages of the natural coagulation cascade to form a structured fibrin clot similar to a physiological clot.

There are several commercial products available (Floseal, Gelfoam, Evicel, Bioglue, surgicel, tachoseal, etc) (3, 5). However, these products have significant limitations, which have prevented their widespread use in cases of severe bleeding in surgery and in emergency medicine, orthopedic and interventional radiology and laparoscopic surgery. All existing haemostatic agents for intracavitary bleeding are designed to be used as adjuncts in light to moderate bleeding and require hard compression. One of the major limitations encountered in the development and/or use of tissue adhesive and sealant compositions for minimally compressible hemorrhage is their inability to form a sufficiently strong bond to tissues when there is profuse bleeding and to produce a stable clot within 10 minutes of application. Therefore, tissue adhesives and sealants have to be employed in combination with compression methods, sutures and/or staples, and adhesive patches so as to reduce the tissue-bonding strength required for acceptable performance. However, there are many situations where the use of strong compression, sutures and/or staples is undesirable, inappropriate or impossible, (e.g. in bone, interventional radiology).

The Present Alternative Approach:

In order to form a physical barrier that resists the flow of blood, the adhesive matrix must form in a matter of seconds a strong fibrin interface, bond with tissues in the midst of flowing blood and remain at the lacerated site to form a clot. The ability to adhere to human tissue of each of the product presentations in a form of a square; a round patch a sphere, a cylinder, or a cone is related to the composition and method of production of fibrin and its interaction (combination) with thrombin to stimulate the coagulatory cascade. The essential aspect of the technology is the ability to bypass the cleavage process of fibrinogen to produce a fibrin monomer and its subsequent polymerized, lyophilized and capable to absorb blood to form a fibrin clot. The agent starts the Clot formation process from an already stabilized I fibrin polymer that absorbs the blood into a lyophilized crosslinked polymer containing the necessary components to stimulate the coagulatory cascade (thrombin) and form a physical barrier that turns into a functional fibrin clot within two minutes of application. (6)

In our approach these results are obtained through a) the application of a polymeric cross-linked lyophilized fibrin network that absorbs the blood forming a very sticky gel-like matrix, which attaches to lacerated tissue; and b) the incorporation of a thrombin layer that contributes to the rapid formation of a strong fibrin clot stabilized by calcium independent transglutaminase enzyme incorporated in the product, and by Factor XIII from the blood.

The lyophilization process in subsequent layers over a biodegradable removable support facilitates its application, and allows for long-term storage, transportation and readiness.

In addition, no fibrin-based products have been developed to address the need arresting hemorrhage from deep cuts or large bed cutaneous wounds, which cause such severe bleeding that often require stitches or sutures.

Composition.

All the forms of the present technology—square, sphere, cylinder or cone incorporate fibrin monomer in acid solution polymerized by a change of pH, which is neutralized by a buffer solution in the presence of activated transglutaminase enzyme (calcium independent) and Factor XIII (calcium dependent) (Calcium dependent and Calcium independent), and calcium chloride. Once fibrin polymer is formed and cross-linked, a second layer of thrombin is incorporated and subsequently lyophilized. (FIG. 1)

The monomer can be mixed with a volume of about 1% to about 5% of glycerol to achieve a specific viscoelastic profile that is adapted to the type of application. The absorption of blood by the cake turns the lyophilized fibrin into a gel, which forms the fibrin clot at sites of injury (7).

Under coagulant conditions, calcium independent transglutaminase and activated Factor XIII from the blood contribute to this process by stabilizing the fibrin clot through covalent bonds.

Key Attributes. Polymerization/Adhesion.

The fibrin gel that seals the wound is formed as a result of the absorption of blood by the lyophilized bilayer material, which maintains covalent bonds while changing from solid to gel state. The clot is mechanically stable, well integrated into the wound and more resistant to lysis by plasmin compared with a non-cross-linked clot [8] or other fibrin sealants. The inclusion of calcium independent transglutaminase facilitates the transglutaminase-mediated cross-linking of the aC-domains polymers in fibrin promoting integrin clustering and thereby increasing cell adhesion and spreading, which stimulates fibrin to bind avb3-, avb5- and a5b1-integrins on endothelial cells [9]. The oligomerization also promotes integrin-dependent cell signaling via focal adhesion kinase (FAK) and extracellular signal-regulated kinase (ERK), which results in an increased cell adhesion and cell migration [10]. The presence of calcium ions enhances the progression from the inflammatory response to the coagulation cascade (first stage) and activates Factor XIII.

The adhesion characteristics to vital human tissue and the kinetics of polymerization of the proposed agent have been tested in vitro and in vivo. The data obtained provide ample evidence of the ability of the various presentation of ClotBlock to stop bleeding and achieve hemostasis with minimal compression in induced intraperitoneal wounds in solid organs or soft tissue. And to stop intramedulary bone bleeding in knee and hip replacement in the swine models.

Lyophilized Fibrin II is obtained from fibrin II monomer polymerization: U.S. patent application Ser. No. 12/487,057 (allowed), which describes a method of preparing a fibrin monomer. The ClotBlock sealant composition uses a lyophilized fibrin polymer obtained from neutralization of fibrin monomer. The composition of parts and method of production of the fibrin II described in this patent application as well as the process of neutralization and crosslinking of the polymer are critical to the performance of the proposed technology which depends on the characteristics of fibrin itself (thickness of the fibers, the number of branch points, the porosity, and the permeability and other polymerization characteristics define clotting factors. The Clot produced by ClotBlock creates opaque matrices of thick fibers, and therefore tube formation proceeds at a faster rate than in transparent matrices. The concentration of thrombin to produce a fibrin monomer and thus the release-rate of FPA also has an important impact on the polymerization process. The described concentrations, dilutions and pH established for ClotBlock produce an optimal fibrin structure at an accelerated rate.

ClotBlock Presentations:

The fibrin polymer can be produced and lyophilized in various sizes, thickness and forms in order to adapt to the type of application (FIG. 2A, 2B, 2C). It can be configured in small spheres or cylinders ¼ inch diameter to be introduced through a laparoscopic port or a vessel in cases on interventional radiology; it can also be molded in round or square flat solid blocks of various sizes in ¼; ½ a 1" thickness for use in spleen laceration, or organ resection, or placed over an adhesive bandage to cover deep skin cuts. The lyophilized form can also be soaked in water and used as a sealing paste or gel.

SUMMARY OF THE INVENTION

The present invention lies within the domain of biological adhesives and tissue sealants, which are biodegradable and nontoxic, intended for therapeutic use, for example, as an adjunct to hemostasis in laparotomy or laparoscopic surgery, or as primary treatment in orthopedic surgery, trauma (spleen laceration), interventional radiology and large-bed wounds.

In one aspect, the present invention relates to biocompatible adhesive fibrin polymer, which is bio-reabsorbable and nontoxic, for surgical or therapeutic use. It also relates to a bilayer application containing bioactive substances, which can be released in a given site to stimulate coagulation. In another aspect, the invention relates to a process for producing such an adhesive polymer.

Extensive in vivo studies show that ClotBlock is an excellent hemostatic agent candidate control moderate to severe bleeding. Its different presentations maximize the hemostatic effect in various types of surgical and trauma applications. The agent is durable, easy to store, poses minimal risk, requires little training to use, and is highly effective against moderate to severe bleeding.

BRIEF DESCRIPTION OF THE DRAWINGS

FIG. 1. ClotBlock layer distribution

FIG. 2 Possible shapes: A Spheres and cylinders; B Patch or Block; C Bandage FIG. 3. Comparison of intratissular adherence strength of Clotcake with Tissel, Floseal, and Evicel.

Figure 3:
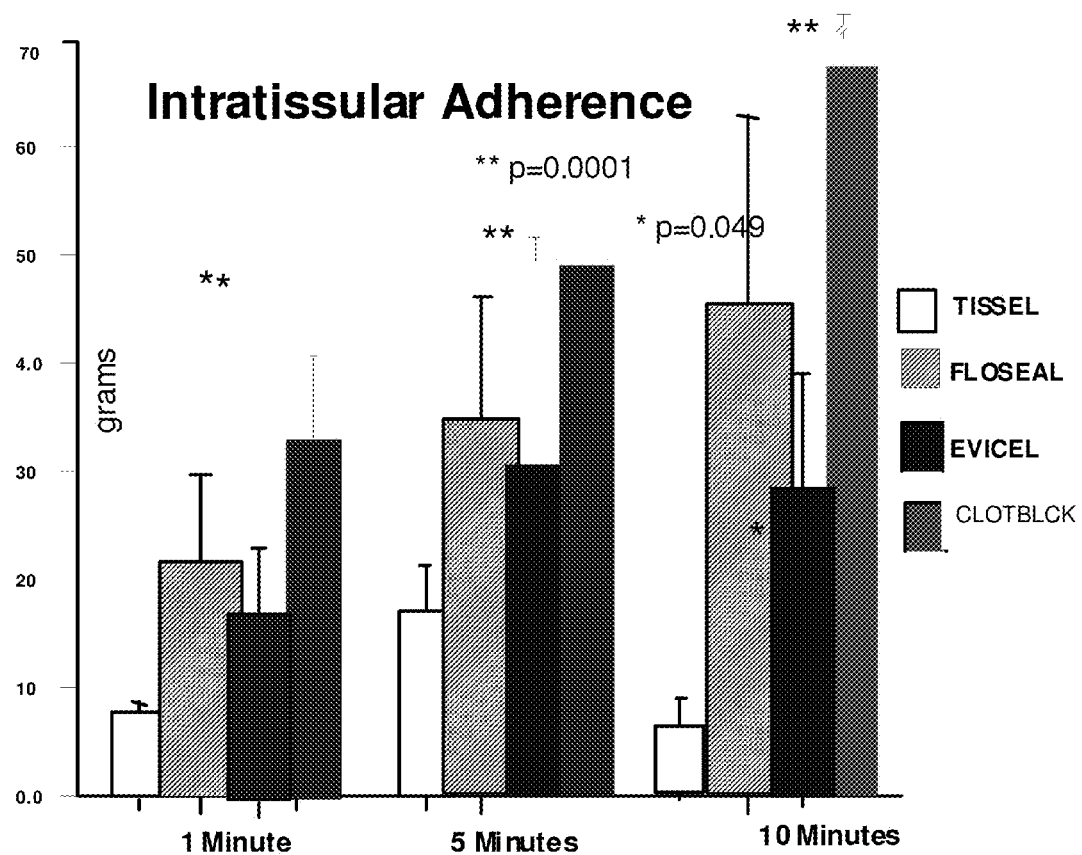

In human fibroblast cultures exposed to ClotBlock preparations a. HF–Untreated b. HF+ClotBlock, Day 5

FIG. 10. Detection of antibodies that might be produced in swine against Thrombin, using a sandwich ELISA (enzyme linked immunosorbent assay).

FIG. 11. Human fibroblast exposed to ClotBlock preparations, there was a total absence of damage or toxicity to the cells, and absence of any bacterial or fungal contamination; the cells appeared slightly larger than in control untreated cultures.
  a. −Untreated, Day 5
  b. fibrioblasts+ClotBlock, Day 5

FIG. 12. Human epithelial cell cultures (A549) exposed to ClotBlock preparations, there was a total absence of damage or toxicity to the cells, and absence of any bacterial or fungal contamination; the cells appeared slightly larger than in control untreated cultures.
  c. A549 cells−Untreated, Day 5
  d. A549 cells+ClotBlock, Day 5

DETAILED DESCRIPTION

We have developed a hemostatic agent that can be shaped in various forms and supports, trademarked as Clotblock. The agent is a novel fibrin sealant (pure fibrin II made by neutralization of fibrin II monomer) supplemented by thrombin, and designed to promote hemostasis in cases of severe bleeding, and to stop hemorrhage with minimal compression resulting from organ resection, trauma and/or solid organ wounds, soft tissue, bone, and large bed wounds. This sealant agent promotes coagulation and provides hemostasis as well as adhesiveness between surfaces of damaged tissue. The present fibrin sealant can be used 1) as an adjunct or as primary treatment for severe bleeding; or 2) shaped for delivery through laparoscopic port or used as a compression in organ resection, or 3) placed on support for use in cases of skin laceration; or 4) shaped to be delivered through catheters in cases of interventional radiology; or 5) shape to seal intramedullary bleeding arising from orthopedic surgery or trauma.

Each of the presentations consists of a lyophilized bilayer (FIG. 1) comprising: 1) a fibrin II polymer produced by neutralization of fibrin monomer in acetic acid solution (pH 3.4) with HEPES buffer (pH 8.3); and crosslinked, by activated Factor XIII and calcium independent tranglutaminase; 2) a layer of thrombin at a concentration of 20 NIH units/ml dissolved in HEPES water solution in a proportion of 1 ml for every 4 ml of fibrin; and 3) the option of adding a third layer PLGA fibronectin embedded microspheres between the fibrin and the thrombin layers.

The lyophilized bilayer is applied over lacerated bleeding tissue, which absorbs the blood to form a sticky, gummy gel barrier and subsequently a fibrin clot as blood is absorbed by the fibrin. 1) The agent seals the wound within 2 minutes, and 2) binds together the lacerated tissue.

ClotBlock has been developed in several formulations, which vary in shape, elasticity, and clotting strength as needed.

Composition and Application

ClotBlock is produced in two layers. It consists of a lyophilized fibrin polymer topped by a layer of lyophilized thrombin. The first layer contains crosslinked fibrin polymer produced by neutralization of fibrin monomer in acetic acid solution mixed with a buffer solution composed of 150 mM NaCl, 50 mM HEPES, 3 mM $CaCl_2$, 0.12 g/mL Activa (calcium independent transglutaminase enzyme) and 21 Lowey Units of Factor XIII per ml of Neutralization buffer, pH 8.5. according to method described in U.S. patent application Ser. No. 12/487,057 and incorporated by reference herein. These two solutions are mixed in a ratio of 1:1 inside a sterile mold. To this Composition 1% to 5% of glycerol can be added, depending on desired flexibility of the block This mold is sealed inside a sterile TYVEK® (Registered trademark of E.I. DuPont Co., Wilmington (DE) bag and incubated at 37° C. for four hours.

The second layer contains a solution of thrombin in a proportion of 1:4 to fibrin, which is dissolved in HEPES buffer at the concentration of 20 units/mL.

Step 1: Each component is sterilized by filtration through a 0.22 micron Millipore filter. Each layer is poured into a silicon mold of the desired shape (round, oval or square) to produce a "cake" of approximately ¾ to 1" thick, which can be supported by a removable or biodegradable polymer of mesh such as polyglactin mesh, or sD,L-lactide polymer synthetic mesh, polylactic acid (PLA)/poly(glycolide-co-lactide) copolymer (PLGA) membrane or polyglycolic acid (PGA) mesh; or by a self-adhesive bandage for use in cases of cutaneous lacerations.

Step 2: Clotblock is then lyophilized at a condenser temperature of −40° C. to −50° C., shelf temperature of 21° C., during 18-72 hours at a pressure of 200-400 millitor.

Step 3: Each piece of ClotBlock is packaged in plastic bags hermetically sealed to prevent moisture loss and maintain sterility.

Step 4: ClotBlock is applied with moderate compression directly over the wound for 1 to 2 minutes. Within 3 minutes a fibrin clot is formed over the wound.

Alternative Delivery Methods:

ClotBlock can be shaped in small cylinders ½" diameter and 1" to 2" long, which can be delivered through a laparoscopic port into an intracavitary wound, or through a catheter to seal a bleeding vessel.

ClotBlock can be dissolved in water at a proportion of 4:2 to form a liquid gel that can be applied with a single syringe on a laceration or wound. ClotBlock can placed over a self-adhesive or non-self adhesive, which is a bi-layer system consisting of flexible fabric adhesive bandage and a sterile biocompatible lyophilized desAB fibrin polymer or fibrin II polymer composition from concentrated desAB fibrin monomer or fibrin II monomer in acid solution, that may be used to stop bleeding or seal cutaneous tissue. This delivery method is particularly related to need of arresting bleeding from large or deep skin cuts by affixing a fibrin Clot compressed by a bandage.

EXAMPLES

The hemostatic characteristics have been tested in animal studies showing that the CLOTBLOCK sealant forms a fibrin clot stronger and faster than other sealants. The adhesive is expected to adhere to lacerated tissue and bind the opposing tissues together with a strength that is significantly higher than that observed for fibrin sealants.

The following laboratory tests were conducted interactively with animal experiments (rat, rabbit and swine models for grade III and IV liver wounds).

1. Ex-Vivo Experiments on Baseline Formulation: Adhesion and Coagulation Properties We conducted adhesion and tensile measurements (Intratissue adherence and clot strength) with an isometric transducer in Sprague-Dawley rat liver tissue.

Figure 5:
FIG. 5. Control of intraoperative bleeding as primary treatment in partial nephrectomy by application of ClotBlock showing the formation of a solid clot within 5 minutes* of application (median of 3.2±1.4 min).

Tensile Measurements:

The two largest lobes of the liver were separated. One lobe was attached to a holder that was fixed later to the isometric transducer. The other lobe was placed in a flat bed of gauze in a container that could gradually be elevated and lowered to produce contact with the piece of liver in the transducer's holder. A damage area of 1 $cm^2$ was produced in both liver pieces. The formulation to be tested for tissue adherence was deposited between the two pieces. The specimens were placed in contact at a baseline pressure of 0 gr. At various time points (1, 5 and 10 minutes of exposure and contact), the pressure needed to completely separate them was recorded. We compared Intratissue adherence of ClotBlock with Tissel, Floseal, and Evicel. The results of the intratissue adherence are depicted in FIG. 5. The force of adherence induced by ClotBlock after 10 min is more than 150% stronger than Evicel and 800% stronger than the control in the intratissue adhesion model (FIG. 3)

2. Molecular Chemistry of Fibrin Polymerization

Figure 4:
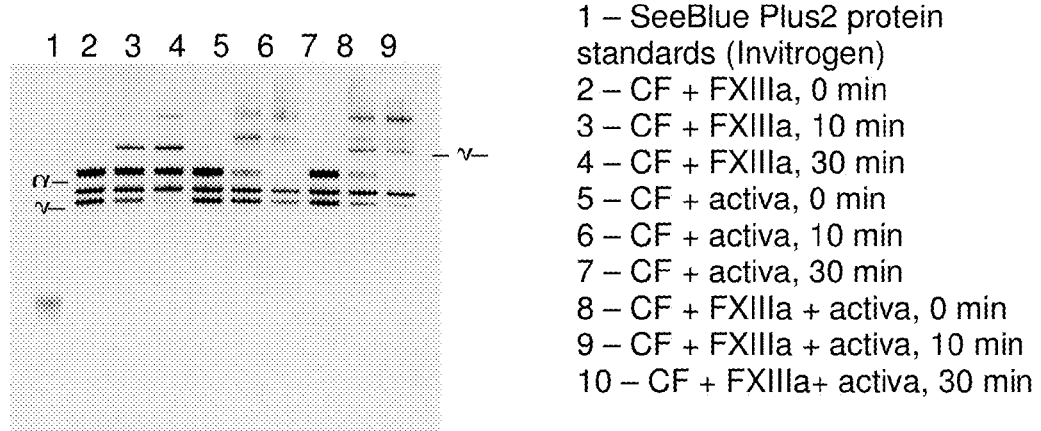
FIG. 4. Polymerization, cross-linking and stabilization of fibrin in the presence of ACTIVA and Activa+Factor XIII.

We conducted molecular chemistry assays to compare the effectiveness of Fibrin monomer polymerization (pH Neutralization) and stabilization (cross-linking) by activated Factor XIII versus Ca Independent tranglutaminase enzyme (FIG. 4).

2.1. Studies to Determine the Effect of ACTIVA on Fibrin Stabilization

It is well established that FXIII in the presence of $Ca^{2+}$ catalyzes fibrin polymer cross-linking resulting in insoluble fibrin clot. However, whether the presence of calcium independent transglutaminase in the reaction mixture catalyzes crosslinking of fibrin was not established. Nor has it been established if there is a synergistic effect of calcium independent transglutaminase and activated Factor XIII. In order to follow these reactions, fibrin was subjected to calcium independent transglutaminase treatment, first as a concentration dependent reaction and later as a time dependant reaction.

Concentration-dependent and time-dependent (1, 5, 10 min) reactions were monitored, A volume of acidic fibrin solution at 2 mg/mL was quickly mixed with Activa in 60 mM Tris buffer (pH 8.4), with 2 mM $CaCl_2$) in variable concentration (1.0-20.0 U/ml) to achieve neutralization. The Fibrin was visualized with anti-fibrinogen antibody (1:50). Assays compared a) fibrin and fibrinogen crosslinking by calcium independent transglutaminase enzyme at 1, 5 and 10 Minutes (FIG. 4) and fibrin crosslinking by calcium independent transglutaminase enzyme at concentrations of 20 u/ml, 19 U/ml, and 1 U/ml.

The figure shows the formation of strong gamma dimmers during fibrin cross-linking with calcium independent transglutaminase enzyme and factor XIII at 1 minute. At this time gamma dimmers are not yet present in the fibrinogen sample.

3. Experiments in Animal Models

We conducted studies on intracavitary intraoperative bleeding in the swine (pig) model in order to assess the Formation of Fibrin Clot by absorption of blood and to the determine the ability to control bleeding.

Study Objectives:

Compare ClotBlock versus standard surgical practice in stopping moderate to severe bleeding during laparoscopic partial nephrectomy; and determine whether the hemostatic is safe and can control intraoperative hemorrhage (minimize intraoperative blood loss).

3.1. Protocol: Evaluation of ClotBlock for the Control of Intraoperative Bleeding as Primary Treatment in Partial Nephrectomy.

Six female Yorkshire crossbred swine, age 2.5 months, weighing 37±2 kg, were used. The protocol was approved by the Institutional Animal Care and Use Committee of TMCI. Animals were subject to a resection of 25% of the kidney via open laparotomy. After the damage was induced, a round block of 2.5" in diameter of 60 CC ClotBlock bi-layer of composition #1F containing 1% glycerol was compressed against the resection in the parenchyma.

Results:

Following a 1-minute profuse bleeding from the interlobular artery, hemostasis was achieved in all six animals (FIG. 5) with the formation of a solid clot within 5 minutes* of application (median of 3.2±1.4 min).

.* The five minute time to hemostasis is defined by the Blood Products Committee of the Food and Drug Administration as the maximum time to demonstrate efficacy in achieving hemostasis.

3.2 Evaluation of ClotBlock for the Control of Spleen Laceration Bleeding as Primary Treatment without Packing or Sutures.

The purpose of this study is to determine if CloBlock can stop profuse bleeding within 5 minutes of application in cases traumatic spleen laceration.

Methods:

Eight female Yorkshire crossbred swine, age 2.5 months, weighing 37±2 kg, were used. The protocol was approved by the Institutional Animal Care and Use Committee.

Figure 6:
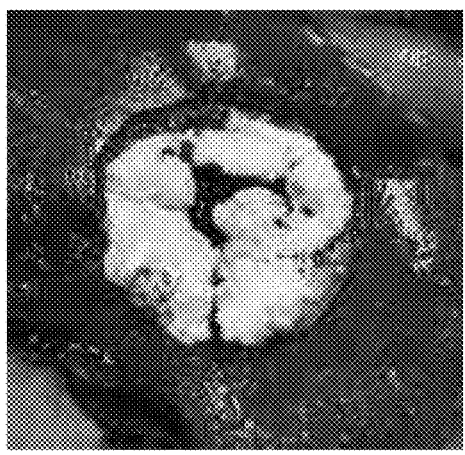
FIG. 6. Control of spleen laceration bleeding as primary treatment without packing or sutures. By application of CloBlock, hemostasis was achieved within 5 minutes of application.

Animals were subject to a 1 inch incision in lateral middle portion of the spleen (created sharply by an 11 blade scalpel). After the damage was induced, a round block of 2.5" in diameter of 60 CC of ClotBlock composition #1F containing 1% glycerol was compressed against the laceration for 2 minutes. Hemostasis was achieved in all animals within 5 minutes of application (FIG. 6).

Results: All animals (n=6) Achieved hemostasis within 5 minutes of application* with a median of 3.2±1.4 min.

* The five minute time to hemostasis is defined by the Blood Products Committee of the Food and Drug Administration as the maximum time to demonstrate efficacy in achieving hemostasis.

3.3 Evaluation of ClotBlock for the Control of Intraoperative Bleeding as Primary Treatment in Liver Injury Grade IV.

Figure 7:
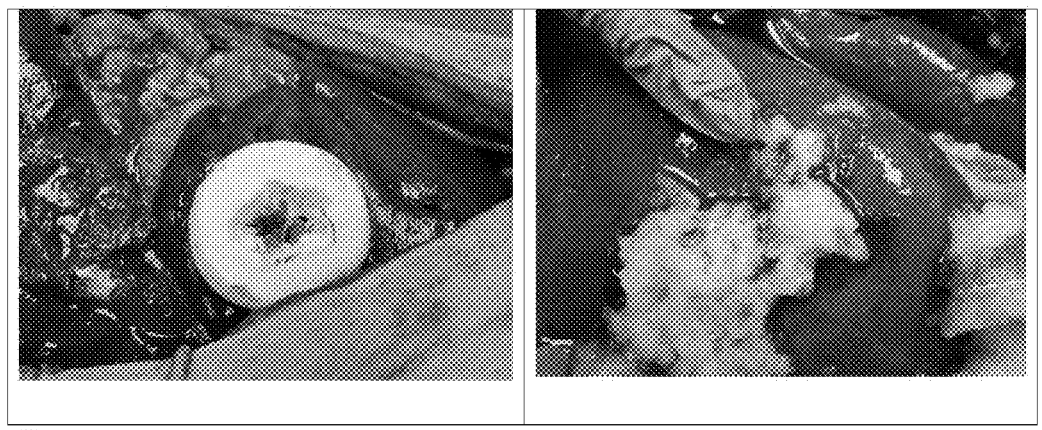
FIG. 7. Control of intraoperative bleeding as primary treatment in liver injury grade IV by application of ClotBlock. Hemostasis was achieved within 5 minutes. Hemostatic effectiveness of ClotBlock in gel form as an adjunct to hemostasis to control intraoperative bleeding in partial hepatectomy. Hemostasis was achieved within 5 minutes of application.

Fourteen female Yorkshire crossbred swine, age 2.5 months, weighing 37±2 kg, were randomized into 3 groups. Group 1 (n=6) consisted of animals who underwent grade 4 liver injuries via open laparotomy and were treated with a 40 CC ClotBlock. Group 2 (n=6) consisted of animals who underwent a similar procedure and were treated with Gel-Foam (Pfizer); and Group 3 (n=4) consisted of animals who underwent a similar procedure, bleeding was stopped by suturing the wound, which was further treated with saline solution. In both hemostatic-treated groups either ClotBlock or Gelfoam was applied and compressed for 2 minutes against the wound. (FIG. 7) For the purposes of this model, a grade 4 injury is defined as a 7 cm long full-thickness parenchyma laceration (created sharply by an 11 blade scalpel). These injuries were consistent with the American Association for the Surgery of Trauma Organ Injury Scaling system.

A spot in the middle of the liver was selected to produce the liver injury with a scalpel. The position was calculated by approximation to the suprahepatic vessels and some branches of the portal vein. The spot was marked with a marker. After the damage was induced, either a 40 CC block of ClotBlock of the patch type treate with Alexa fluorescent dye with a PLGA membrane as support or a 3×3 inch piece of GelFoam was compressed was against the wound for 2 minutes.

Fluid resuscitation with Lactated Ringer's (LR) was begun immediately after injury. LR was infused as necessary to re-establish a MAP within at least 80% of the pre-injury MAP if possible. Resuscitation was continued for the entire observation period. At the end of the 60 minute study, each animal's MAP and the total resuscitation volume infused were recorded.

All animals in group 2 (Gelfoam) were euthanized after this procedure was complete. Half of Animals in Group 1 (Clotblock n=3) and Group 3 (Control saline n=2) were euthanized at 2 weeks of completion of the study, and the other haLf (Group 1 n=3 and Group 3 n=2) were euthanized at 4 weeks after completion. Necropsy was performed and histological samples were obtained from several organs Outcome Measures Primary Endpoints:

Proportion of successes achieving hemostasis within 5 minutes following injury. The pre-specified primary endpoint is the time to hemostasis, defined as the time interval from application to termination of bleeding or oozing from the parenchyma. If recurrent bleeding from the sheath site occurred following initial hemostasis, the timing and duration of additional non-compressible application required to reestablish complete hemostasis was also recorded.

Secondary endpoints Total blood loss and amount of resuscitation fluid required to maintain Median Blood Pressure within 10% of baseline.

Results:

End points for animals in Groups 1 and 2 (Grade IV injuries) are shown in Table 1. Outcome measures for Grade IV liver injuries treated with ClotBlock (Group 1) and with Gel-Foam (Group 2). All values reported as mean±SEM

TABLE 1

| Group | Survival Time (min) | Total Blood Loss (ml) | Hemostasis at Min 5 | Fluid Requirement (ml) |
|---|---|---|---|---|
| 1 (n = 6) | 60 ± 0 | 100 ± 83 | 5 | 200 ± 83 |
| 2 (n = 6) | 60 ± 0 | 300 ± 112 | 0 | 775 ± 342 |
| 3 (n = 4) | 60 ± 0 | 210 ± 60 | 5 | 400 ± 93 |

Conclusion:

All animals treated with ClotBlock achieved hemostasis within 5 minutes of application. ClotBlock significantly decreases the bleeding time and blood loss, and significantly improves the adhesion between lacerated and damaged tissue.

3.4. Evaluation of ClotBlock Placed Over a Self-Adhesive Bandage for the Control of Severe Cutaneous Bleeding as Primary Treatment.

Ten female Yorkshire crossbred swine, age 2.5 months, weighing 37±2 kg, were randomized into groups. Group 1 (n=5) consisted of animals who underwent a deep shin laceration 3" long in the groin injuries and treated with ClotBlock placed over a self-adhesive bandage for 10 minutes. Group 2 (n=5) consisted of animals that underwent a similar procedure and were not treated.

Outcome Measures

Primary Endpoints:

Proportion of successes achieving hemostasis within 10 minutes following injury. Secondary endpoints Total blood loss Results:

End points for animals in Groups 1 and 2 are shown in Table 2. All values reported as mean±SEM

TABLE 2

| Group | Total Blood Loss (ml) | Hemostasis at Min 10 |
|---|---|---|
| 1 (n = 5) | 20 ± 13 | 5 |
| 2 (n = 5) | 210 ± 112 | 0 |

Conclusion:

All animals treated with ClotBlock in a bandage form achieved hemostasis within 10 minutes of application. ClotBlock significantly decreases the bleeding time and blood loss, and significantly improves the adhesion between lacerated and damaged tissue.

4. Safety Studies

Three out of the six swine, Group 1 (n=6) who underwent grade 4 liver injuries via open laparotomy and were treated with a 40 CC ClotBlock block were euthanized at week two after completion of surgery, and the remaining three at 4 weeks. Similarly, two controls (group 3) were followed and euthanized after 2 weeks, and two animals were euthanized after 4 weeks. Necropsy was performed and tissue samples from main organs were obtained.

The safety of the agent was assessed through the evaluation of toxicity, physiological adverse effects, biocompatibility, delayed hematoma and/or edema formation and immunological risks. Physiological and pathological observations included: Mortality/morbidity; Body weight, Food consumption, Organ weights:

4.1 Acute Toxicity was assessed by macroscopic evaluation at necropsy and by histological studies. Irritation of tissues and tissue vessels to which the agents ere in contact was assessed looking for evidence of acute and/or chronic inflammation as signs or irritation in the histology. Thrombosis, fistula, and abscess formation was assessed for all organs 4.2 Assessment of Delayed Hematoma:

Risk of subcapsular or parenchymal hematoma formation. Delayed hematoma and edema formation was observed macroscopically and histologically at 21 days after application. Small hematoma formation is defined as a visible or palpable mass of ≤4 cm in diameter without associated sequelae.

4.3. Gross pathology and Histology

We analyzed the histological damage in lungs, kidneys, liver, spleen from all treated after 2 and 4 weeks of surgery, and compared sample treated with ClotBlock to control (treated with saline solution) Data on inflammation included apoptosis and leukocyte infiltration. Inflammation and edema formation was also assessed histologically Once animals are sacrificed, organs were collected, fixed in 10% formalin and embedded in paraffin blocks. Histologic sections were stained with Hematoxylin and Eosin and examined at 100× and 400× in optical and microscopes. These slides were evaluated by a Board-certified veterinary pathologist as shown in table 3.

Results:

TABLE 3

TDMI PROTOCOL No: 09-019 4-week follow-up

| ANIMAL ID | TISSUE | MORPHOLOGIC DIAGNOSES |
|---|---|---|
| #04373 | Liver | 1. Peritonitis, mild, chronic, focal, pleocellular (granulomatous, neutrophilic, lymphoplasmacytic, eosinophilic) with fibrosis, subcapsular hepatitis and foreign material |
| Treated | | 2. Hepatitis, periportal, minimal to mild, chronic, lymphoplasmacytic, |

TABLE 3-continued

TDMI PROTOCOL No: 09-019 4-week follow-up

| ANIMAL ID | TISSUE | MORPHOLOGIC DIAGNOSES |
|---|---|---|
| | | eosinophilic<br>3. Lipidosis, microvesicular, minimal, diffuse |
| | Lung | none |
| | Kidney | 1. Nephritis, interstitial, mild, chronic, multifocal, lymphoplasmacytic |
| | Liver injury site | 1. Peritonitis, mild to moderate, pleocellular (granulomatous, neutrophilic, lymphoplasmacytic, eosinophilic) with fibrosis, subcapsular hepatitis<br>2. Hepatitis, periportal, minimal to mild, chronic, diffuse, ymphoplasmacytic and eosinophilic<br>3. Lipidosis, microvesicular, minimal to mild, diffuse |

Summary of Morphologic Diagnoses:

Heart:

No significant findings

Lung:

1. Atelectasis, mild to moderate, multifocal

2. Edema, minimal to mild, acute, diffuse

3. Hemaglobin crystals, minimal, focal, with mild neutrophilic inflammation

Kidney:

1. Granular casts, intratubular, minimal, multifocal

2. Hyaline droplets, intracytoplasmic, proximal tubular epithelium, minimal to mild, multifocal Abdominal Wall:

Fibrous tract, focal, with a central cavity, mild to moderate granulomatous, neutrophilic, lymphoplasmacytic inflammation with hair shafts, and moderate edema Gross Pathology finding are summarized in table 4.

TABLE 4

| Pig Number And procedure | Treatment | General Condition at Necropsy | Adhesions | Other organs | Hematoma |
|---|---|---|---|---|---|
| #04362<br>Grade IV<br>Liver Injury,<br>no suture<br>(2 weeks) | 40 cc<br>ClotBlock<br>#1F Primary<br>treatment<br>2 min<br>compression | normal | Moderate adhesions from abdominal wall and on liver | 1 Implant growth on small bowel 2. All else normal | No hematoma |
| #04366<br>Grade IV<br>Liver Injury,<br>no suture<br>(2 weeks) | 40 cc<br>ClotBlock<br>#1F Primary<br>treatment<br>2 min<br>compression | normal | None | All normal | No hematoma |
| #04372<br>Grade IV<br>Liver Injury,<br>no suture<br>(2 weeks) | 40 cc<br>ClotBlock<br>#1F Primary<br>treatment<br>2 min<br>compression | Normal | 1. some adhesions from abdominal wall to organs<br>2. Dense liver adhesions | All else normal | No hematoma |
| #04373<br>Grade IV<br>Liver Injury,<br>no suture<br>(4 weeks) | 40 cc<br>ClotBlock<br>#1F Primary<br>treatment<br>2 min<br>compression | 1. suture granuloma | 1. dense adhesions from abdominal wall to liver and spleen<br>2. adhesions on spleen | All else normal | No hematoma |
| #04376<br>Grade IV<br>Liver Injury,<br>no suture<br>(4 weeks) | 40 cc<br>ClotBlock<br>#1F Primary<br>treatment<br>2 min<br>compression | normal | 1. moderate adhesions to abdominal wall<br>2. some adhesions on spleen<br>3. some adhesions on liver | All else normal | No hematoma |
| #04377<br>Grade IV<br>Liver Injury,<br>no suture<br>(4 weeks) | 40 cc<br>ClotBlock<br>#1F Primary<br>treatment<br>2 min<br>compression | normal | 1. moderate adhesions to abdominal wall<br>2. some adhesions on spleen<br>3. some adhesions on liver | All else normal | No hematoma |

Conclusion:

Both the control (sutured) and non-sutured treated animals contained mild chronic inflammation and fibrosis at the site of the abdominal wall injury. Only the treated animals had evidence of granulomatous inflammation associated with foreign material (ClotBlock), at the abdominal wall injury site, hepatic injury site and seeding adjacent peritoneal surfaces. While treated animals did not show histologic evidence of notable hemorrhage at either clinical location, sutured controls presented evidence of severe Peritonitis and subcapsular hepatitis, and hematoma with necrosis and fibrosis. There was no evidence of thromboembolism in any other organ. The control animals had evidence of extramedullary hematopoiesis in the spleen, interpreted as a response to hemorrhage from previous surgical injury. No changes to suggest significant blood-loss anemia was seen in either animal.

All pigs, treated and control developed adhesions when wounded and treated or sutured. Therefore adhesions are not caused by ClotBlock, although ClotBlock as other fibrin sealants may be a contributing factor.

4.4. Pharmacokinetic Profile of the Agent Through Biodegradation Studies.

Elimination through biodegradation by proteolytic enzymes was determined in vivo.

Method:

To examine the fate of ClotFoam in vivo, a batch of ClotBlock was prepared using fluorescein-tagged human fibrinogen as tracer. This preparation of ClotBlock was applied to the six animals of Group 1 in the liver grade IV wound procedure (4.3), which were euthnanized at 2 weeks (n=3) and 4 weeks (n=3) following application. Once animals are sacrificed, organs were collected, fixed in 10% formalin and embedded in paraffin blocks. Histologic sections were examined at 100× and 400× in fluorescence microscope. The elimination of ClotBlock was determined by either the total absence of fluorescent traces in the samples, or by the level of fluorescense observed at 2 weeks and 4 weeks.

Figure 8:
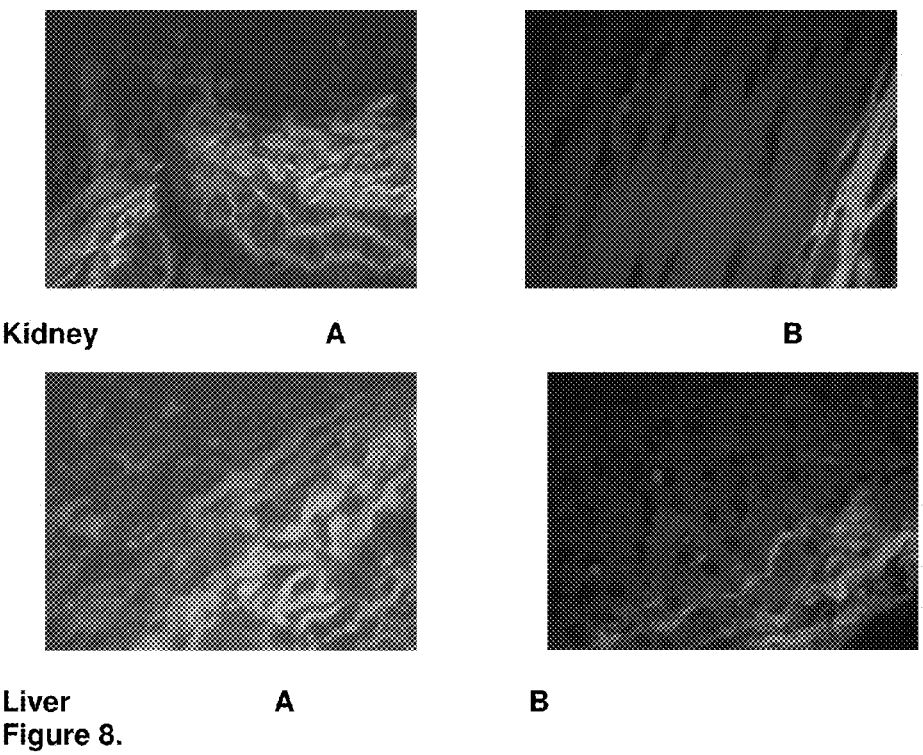
FIG. 8. Microscopic examination under UV light comparing the trace in fluorescence trapped in interstitial spaces in kidney and liver at 2 weeks (A) with 5 weeks (B) after application.

Results:

Clotblock was eliminated in all organs within 4 weeks of application (FIG. 8)

4.5. Evaluation of Immunologic Response

Potential antibody responses to ClotBlock were evaluated.

Methods: Serum samples were collected from experimental animals subjected to liver grade IV injury (4.3), pre- and post-treatment on Day 0, Day 7, and Day 21 days post-surgery and stored frozen at −20° C. until analysis. Antibodies generated to the components that are used in the formulation of ClotBlock were tested by enzyme-linked immunosorbent assay (ELISA).

To detect antibodies that might be produced in swine against components of ClotBlock, a sandwich ELISA (enzyme linked immunosorbent assay) was constructed. The bottom surfaces of 96-well microtiter plates were coated overnight at 4° C. with Fibrin (10 mg/ml in PBS, pH 7.0, Sigma-Aldrich) or thrombin (n 10 mg/ml in PBS, pH 7.0, Sigma-Aldrich). All wells were washed 5 times with PBS. Samples of swine serum were applied at 1:20 final dilution in PBS, incubated for 1 hr at room temperature and washed 5 times with PBS. Enzyme (horseradish peroxidase)—conjugated rabbit antibodies to pig IgG (Sigma-Aldrich) were applied to all wells at 1:20 dilution in PBS, incubated for 1 hr at room temperature, and washed 5 times with PBS. Substrate was prepared by dissolving one capsule of substrate (2,2'-Azino-bis(3-ethylbenzothiazoline-6-sulfonic acid) di-ammonium salt, 10 mg/capsule, Sigma-Aldrich) in 100 ml of phosphate-citrate buffer, pH 5.0, and adding $H_2O_2$ (0.25 ml of 3% solution). Following incubation for 10 min at room temperature, optical density at 405 nm was determined using a BioTek EX800 microplate reader.

Each targeted component was diluted 1:100 in phosphate-buffered saline (PBS), pH 7.4, coated onto microtiter plate wells, and incubated overnight at 4° C. The wells were blocked with 0.25% (wt/vol) nonfat dry milk/0.2% Tween 20 in PBS (blocking buffer) and then incubated with 50 μL of a 1:10 dilution of animal serum in blocking buffer for 1 hour at 37° C. Bound IgG and IgM were detected as standard ELISA system for secondary antibody.

The normal range was determined with 5 normal animal sera. An elevated antibody level is defined as greater than two standard deviations above the normal mean. Each plate included wells incubated with all reagents except for the diluted serum, which provided the background absorbance that was subtracted from all results. Antibodies to purified thrombin were determined as described for antibodies to prothrombin, except that purified thrombin (5 μg/mL) was used to coat the microtiter plate wells. Inhibitory anti-factor V antibodies binding to the factor V C2 domain are associated with hemorrhagic manifestations. Antibodies to human factor V were identified by coating microtiter plate wells with the murine monoclonal antihuman factor V antibody 6A5 (50 μL of 2.5 μg/mL overnight at 4° C.). The wells were washed and blocked, after which they will were incubated with 50 μL of 5 μg/mL human factor V. The wells were incubated with a 1:10 dilution of animal plasma for 1 hour at 37° C. Bound IgG was detected as described above (standard sandwich ELISA).

It is very important to consider that then present is a cross species model zymogenic system with human components being tested in rats and swine. Even if the animal produces antibodies against any of ClotBlock components, it is not certain that results could be extrapolated to human. There is not a homologous experimental system at the preclinical stage.

Statistical Analysis

A comparison of the quantitative variables among the 6 randomized subgroups within the two treatment arms will performed using the Kruskall-Wallis test. The Mann-Whitney U test will used to assess the differences between each randomized group. Statistical analyses were conducted using Stata, version 9.0 (Stata, College Station, Tex.), with P<0.05 considered statistically significant.

Figure 9:
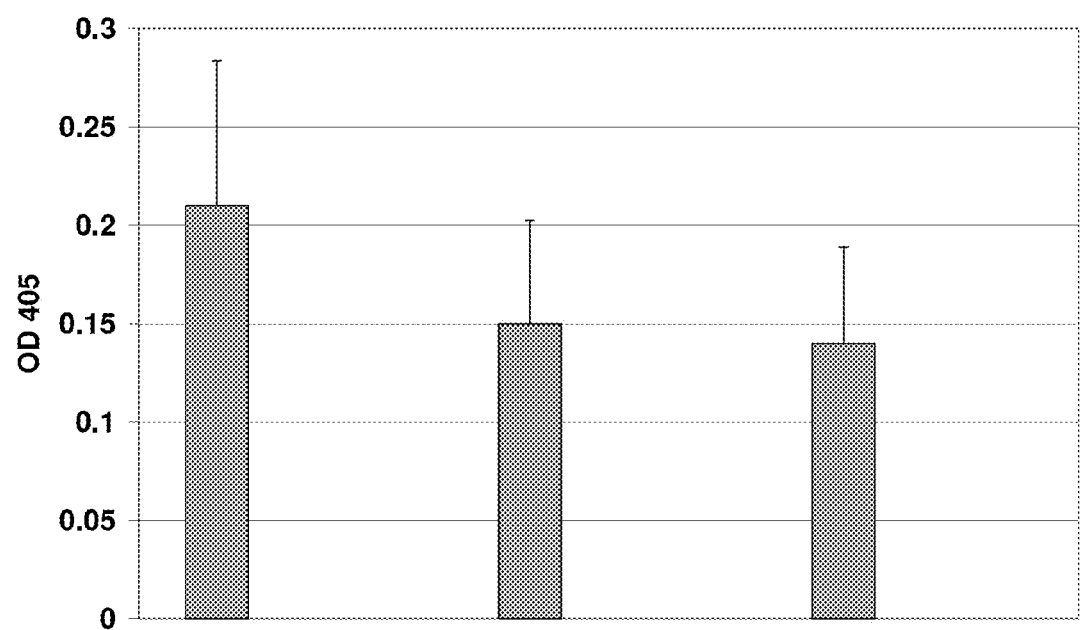
FIG. 9. Detection of antibodies that might be produced in swine against Thrombin, using a sandwich ELISA (enzyme linked immunosorbent assay).

Results and Conclusion:

There were no significant differences in OD readings observed with sera collected on day 0, day 7 or day 21 from control and ClotBlock treated pigs when tested against Fibrin or Thrombin (FIGS. 9 and 10). We conclude that experimental pigs produced no detectable antibodies against ClotBlock.

5. Sterilization

Sterile preparations of clotcake were studied.

The acidic Fibrin Monomer was sterile filtered in a biological safety cabinet using a Nalg-Nunc 500 mL device (Cat #450-0045, nitrocellulose membrane, 0.45 m filter).

Growth Study:

The general experimental protocol included preparation of sample solutions which were then plated on Potato dextrose agar (PDA, Sigma-Aldrich, Cat#P2182) and Tryptic soy agar (TSA, Sigma-Aldrich, Cat# T4536) gels in Petri dishes for growth. The PDA and TSA gels were incubated and observed at the indicated periods of time for colony growth (mold and/or bacteria).

The sample was incubated for 30 min at 37° C. and evaluated for colony growth using the naked eye at the time periods indicated in the Results and Discussion section. The samples were run in duplicate or triplicate with multiple samples indicated with a 1, 2 and 3 designation in data tables. The scale used for evaluation is as follows:

TABLE 2

Colony Count Key

| Symbol | Count |
|---|---|
| — | No visible growth |
| + | 1-199 visible colonies |
| ++ | 200-399 visible colonies |
| +++ | >400 visible colonies |

TABLE 3 shows the results of studies of microorganism growth analysis on PDA and TSA of the sterile components of FIBRIN_ClotFoam.
Sterilization Studies by Bacterial Growth on PDA/TSA at 37° C.

| | | Potato Dextrose Agar (PDA) | | | | | | | Tryptic Soy Agar (TSA) | | | | | | |
|---|---|---|---|---|---|---|---|---|---|---|---|---|---|---|---|
| Time Elapsed (days) | | 1 | 2 | 3 | 4 | 5 | 6 | 7 | 11 | 1 | 2 | 3 | 4 | 5 | 6 | 7 | 11 |
| Sample | #s$ | | | | | | | | | | | | | | | | |
| C** | 1 | | | | — | | | — | — | | | | — | | | — | — |
| (Fibrin/AcOH, | 2 | | | | — | | | — | — | | | | — | | | — | — |
| pH 3.5) | 3 | | | | \! | | | — | — | | | | — | | | — | — |

**"sterile" C used for animal studies in SUNY, stored at 4° C. for a week

The growth data indicate that sterile components yielded no significant growth even after 11 days. Furthermore, the following techniques could be used for sterilization.

6. Biocompatibility

Two ClottBlock preparations were prepared and tested under sterile conditions. These preparations were tested for biocompatibility with human fibroblasts (HF) and human epithelial cells (A549 cell line, ATCC).

Normal human fibroblasts (HFs) were obtained from a commercial source and cultures established in 60 mm tissue culture plates in Dulbecco's modified Eagle's medium supplemented with 10% fetal bovine serum and maintained at 37° C. in a humidified 5% $CO_2$ atmosphere ($CO_2$ incubator). Human epithelial cell line A549 was maintained in Minimal Essential Medium supplemented with 10% fetal bovine serum and 2 mM glutamine. When fibroblast and epithelial cell cultures reached subconfluence, control and sodium benzoate ClotFoam preparations were mixed and immediately delivered into individual dishes. The cultures were returned to the $CO_2$ incubator and examined daily for a total of five days. ClotFoam material and medium was removed from all cultures, and adherent cells were stained with crystal violet (0.1% in 2% ethanol).

Results:

The main observation was a total absence of damage or toxicity to the cells, and absence of any bacterial or fungal contamination.

In human fibroblast cultures exposed to ClotBlock preparations, the cells appeared slightly larger or more spread out than in control untreated cultures. FIG. 11(, b,) and well as in human epithelial cells FIG. 12,(a, b,)

Conclusion:

ClotBlock is biocompatible, and does not inhibit, but rather stimulate, the growth and differentiation of cells; which is an important attribute in wound healing agents.

LITERATURE CITED

1. Mosher D F, Schad P E. Cross-linking of fibronectin to collagen by blood coagulation Factor XIIIa. J Clin Invest. 64:781-7. 1979.
2. Rousou J, Levitsky S, Gonzalez-Lavin L. Cosgrove D, Magilligan D, Weldon C, Hiebert C, Hess P, Joyce L, Bergsiand J, et al. Randomized clinical trial of fibrin sealant in patients undergoing resternotomy or reoperation after cardiac operations. A multicenter study. J Thorac Cardiovasc Surg. 97:194-203. 1989
3. Dunn C J, Goa K L, Fibrin sealant: a review of its use in surgery and endoscopy. Drugs. 58:863-86. 1999
4. Schelling G, Block T, Gokel M, Blanke E, Hammer C, Brendel W. Application of a fibrinogen-thrombin-collagen-based hemostatic agent in experimental injuries of liver and spleen. *J Trauma*, 28:472-5. 1988.
5. Biggs G, ClotFoamron J, Feliciano J, Hoenig D M. Treatment of splenic injury during laparoscopic nephrectomy with BioGlue, a surgical adhesive. Urology. 66:882. 2005.
18. Platelet Protocols. Research and Clinical Laboratory Procedures. McCabe White M. and Jennings L. K. Academic Press, 1999.
6. (Fang N, Zhu A, Chan-Park M B, Chan V. Adhesion contact dynamics of fibroblasts on biomacromolecular surfaces. *Macromol Biosci.* 2005 Oct. 20; 5(10):1022-31.)
7 Action of fibrinogen degradation products and fibrin monomer soluble complexes on platelet aggregation. Larrieu M J. Scand J Haematol Suppl. 1971; 13:273-9.
8. Francis C W, Marder V J. Increased resistance to plasmic degradation of fibrin with highly crosslinked alpha-polymer chains formed at high factor XIII concentrations. *Blood.* 1988 May; 71(5):1361-5
9. Okumura N, Terasawa F, Haneishi A, Fujihara N, Hirota-Kawadobora M, Yamauchi K, Ota H, Lord S T. B:b interactions are essential for polymerization of variant fibrinogens with impaired holes 'a'. J Thromb Haemost. 2007 December; 5(12):2352-9. Epub 2007 Oct. 8
10. Ozeki M, Tabata Y. In vivo degradability of hydrogels prepared from different gelatins by various cross-linking methods. J Biomater Sci Polym Ed. 2005; 16(5):549-61.
11. Belitser V A, Varetskaja T V, Malneva G V. Fibrinogen-fibrin interaction. Biochim Biophys Acta. 1968 Feb. 19; 154(2):367-75

What is claimed is:

1. A sterile polymeric cross-linked lyophilized fibrin network composition forming an adhesive gel matrix, which attaches to lacerated tissue for the control of bleeding, the composition consisting of:
  a) a layer of ¼ to 1" thickness of lyophilized crosslinked desAB fibrin (fibrin II) polymer, b) a layer of lyophilized thrombin, c) an optional support layer of non-removable self-adhesive bandage, or hyaluronic acid, or removable mesh made of a biodegradable polymer.

2. The composition as claimed in claim 1, wherein the fibrin polymer is made by reaction of a desAB fibrin monomer with a neutralization buffer, the neutralization buffer being added in a 1:1 by volume ratio.

3. The composition as claimed in claim 2, wherein the crosslinked fibrin further comprises about 1% to 5% glycerol added before lyophilization on a volume-volume basis.

4. The composition as claimed in claim 2, wherein the neutralization buffer used to polymerize the monomer and crosslink the fibrin comprises:

150 mM NaCl 50 mM HEPES 3 mM $CaCl_2$ 0.12 g/mL of stabilized calcium independent transglutaminase enzyme (Activa) and 21 Lowey Units of Factor XIII per ml of neutralization buffer.

5. The neutralization buffer as claimed in claim 4 wherein the buffer has a pH of 8.5.

6. The composition claimed in claim 2 wherein the fibrin polymer is crosslinked by a calcium independent transglutaminase enzyme mixed into the neutralization buffer.

7. The composition as claimed in claim 1, wherein the composition is characterized as not interfering with the growth of human fibroblasts, or as being biocompatible, as well as non-toxic, non-immunogenic, and safe for use in humans.

8. The composition as claimed in claim 1, when is applied to a bleeding wounded tissue, absorbs the blood forming a gel that effects the formation of a stable fibrin clot over the wound.

9. The composition as claimed in claim 8 wherein hemostasis to control moderate to severe bleeding is optionally achieved as primary treatment without packing or sutures or as an adjunct to hemostasis within five minutes of application of the composition to the wounded tissue.

10. A composition as claimed in claim 1 wherein the layers are optionally organized with or without a support.

11. The composition as claimed in claim 1, wherein the adhesive support is made of material selected from the group consisting of hyaluronic acid and a biodegradable polymer including polyglactin mesh, or D,L-lactide polymer synthetic mesh, polylactic acid (PLA)/poly(glycolide-co-lactide) copolymer (PLGA) membrane or polyglycolic acid (PGA) mesh.

12. A composition as claimed in claim 1 wherein the adhesive support used to stop cutaneous bleeding can optionally be made of a layer of non-removable self-adhesive bandage of the type of sterile flexible fabric self-adhesive bandage.

13. A method to produce a fibrin sealant composition for control of bleeding with or without compression comprising the steps of:

a) forming a layer of desAB fibrin polymer;

b) forming a layer of thrombin;

c) adding an optional support layer of non-removable self-adhesive bandage, hyaluronic acid, or removable mesh made of a biodegradable polymer.

14. The method as claimed in claim 13, further comprising the step of reacting a fibrin monomer with a neutralization buffer, the buffer being added in a 1:1 ratio to the fibrin monomer.

15. The method as claimed in claim 14, further comprising the step of mixing the fibrin monomer and the neutralization buffer with or without the optional layers in a mold.

16. The method as described in claim 14, wherein the neutralization buffer comprises:

150 mM NaCl, 50 mM HEPES, 3 mM $CaCl_2$, 0.12 g/mL of stabilized calcium independent transglutaminase enzyme (ACTIVA); and 21 Lowey Units of Factor XIII per ml of neutralization buffer.

17. The method as claimed in claim 14, further comprising the step of adding glycerol to the fibrin monomer in a concentration ranging from about 1% to about 5%.

18. The method as claimed in claim 14, wherein the neutralization buffer has a pH of 8.5.

19. The method as claimed in claim 14, wherein the fibrin polymer is crosslinked using a calcium independent transglutaminase enzyme.

20. The composition as claimed in claim 1 wherein the layers are lyophilized under sterile conditions with or without support in molds having various shapes, thickness and sizes—square, sphere, cylinder or cone—as to adapt to the surgical indication.

21. The composition as claimed in claim 12 wherein the adhesive support is optionally removed after application over a bleeding wound in order to seal tissue and control vascular, epidermal, or internal hemorrhage.

* * * * *